United States Patent [19]

Dummer et al.

[11] Patent Number: 4,822,932
[45] Date of Patent: Apr. 18, 1989

[54] HEAT RECOVERY IN PRODUCTION OF VINYL CHLORIDE BY PYROLYSIS OF DICHLOROETHANE

[75] Inventors: Gerhard Dummer, Burgkirchen; Klaus Haselwarter, Burghausen; Hermann Klaus, Markt; Ludwig Schmidhammer, Haiming; Rudolf Strasser, Burghausen, all of Fed. Rep. of Germany

[73] Assignee: Wacker-Chemie GmbH, Fed. Rep. of Germany

[21] Appl. No.: 178,477

[22] Filed: Apr. 7, 1988

Related U.S. Application Data

[63] Continuation-in-part of Ser. No. 937,710, Dec. 4, 1986, abandoned, which is a continuation of Ser. No. 779,256, Sep. 23, 1985, abandoned.

[30] Foreign Application Priority Data

Nov. 9, 1984 [DE] Fed. Rep. of Germany ....... 3441080

[51] Int. Cl.$^4$ ...................... C07C 17/24; C07C 17/34; C07C 21/06
[52] U.S. Cl. ...................... 570/226; 570/238
[58] Field of Search ................. 570/226, 238

[56] References Cited

U.S. PATENT DOCUMENTS

| | | | |
|---|---|---|---|
| 2,724,006 | 11/1955 | Krekeler | 570/226 |
| 3,655,787 | 4/1972 | Wiley | 570/238 |
| 3,761,136 | 9/1973 | Wall | 570/238 |
| 4,324,932 | 4/1982 | Link et al. | 570/226 |

FOREIGN PATENT DOCUMENTS 1127669   7/1982   Canada ................ 570/226

Primary Examiner—J. E. Evans
Attorney, Agent, or Firm—Bierman and Muserlian

[57] ABSTRACT

In a method of treating the reaction product of pyrolysis of 1,2-dichloroethane to form vinyl chloride and hydrogen chloride with multiple stage cooling and distillation separation of the reaction product and recycle of unreacted 1,2-dichloroethane to the pyrolysis step, the improvement comprising direct cooling of the reaction product immediately after leaving the pyrolysis step, within 1 sec from a temperature range of 480° to 540° C. down to 150° to 250° C., charging the cooled product into a quench column, recovering the vapors from the head of the quench column and indirectly cooling the same by heat exchange to at least its condensation point, the heat exchange media being at least one member of the group consisting of (a) 1,2-dichloroethane to be fed in heated condition to the pyrolysis unit, (b) air used as combustion air to fire the pyrolysis zone, (c) the sump of the hydrogen chloride column as defined above, (d) liquid hydrogene chloride to be evaporated and, (e) water, to dissipate heat not used within the measures according to the present invention.

1 Claim, 1 Drawing Sheet

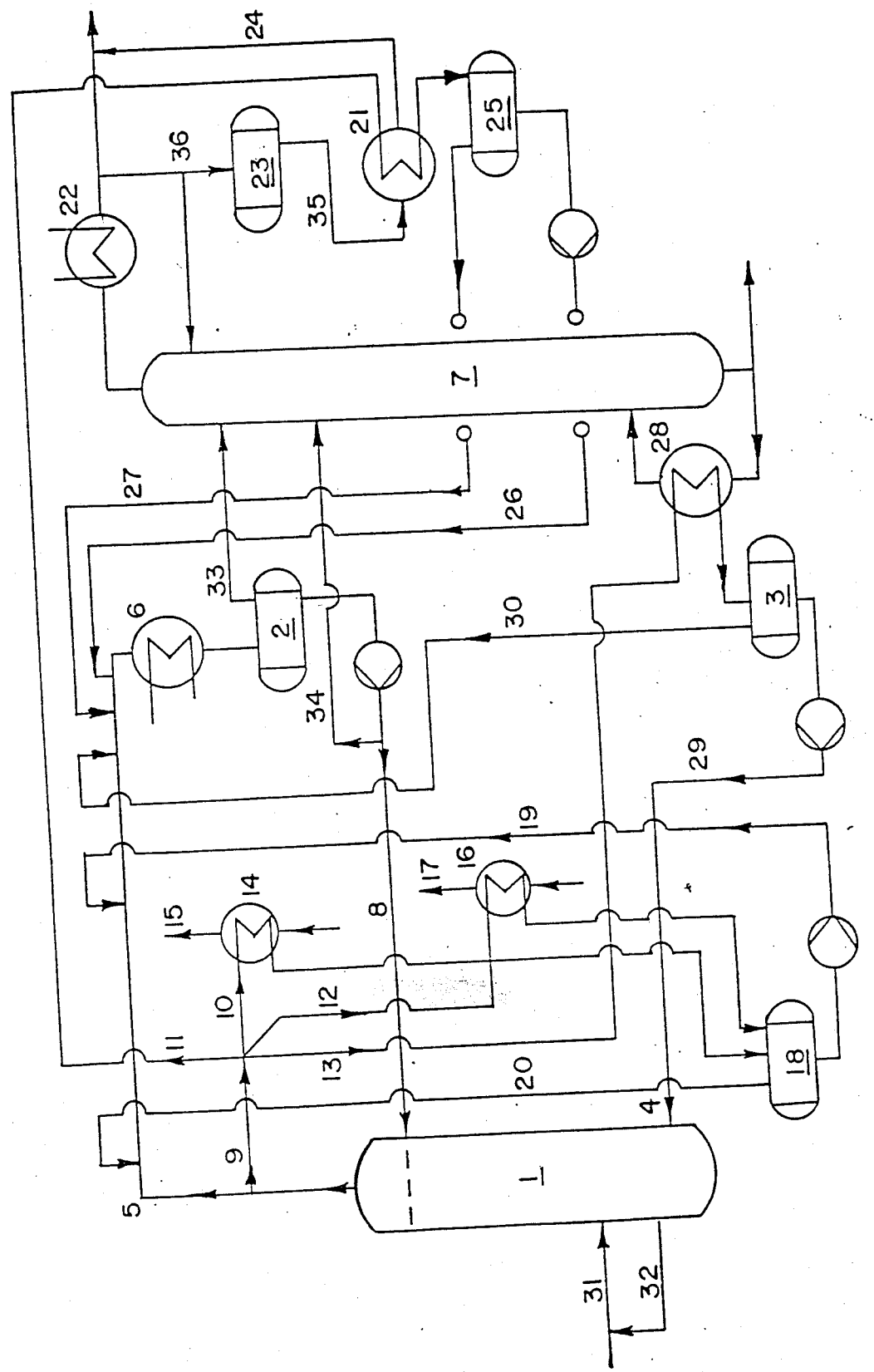

HEAT RECOVERY IN PRODUCTION OF VINYL CHLORIDE BY PYROLYSIS OF DICHLOROETHANE

PRIOR APPLICATION

This application is a CIP of copending application Ser. No. 937,710 filed Dec. 4, 1986 which in turn is a continuation of U.S. patent application Ser. No. 779,256 filed Sept. 23, 1985, both now abandoned.

STATE OF THE ART

The industrial production of vinyl chloride by pyrolysis of 1,2-dichloroethane and subsequent separation of the reaction product by distillation into its main-components, hydrogen chloride and vinyl chloride and unreacted 1,2-dichloroethane is known.

This process requires approximately 0.3 to 0.4 giga Joule per 100 kg of vinyl chloride produced and the great majority of this energy develops primarily as heat content of the pyrolysis product leaving the pyrolysis zone. The great majority of the said heat must be dissipated again as quickly as possible to suppress the formation of by-products and prevent corrosion damage to the equipment. Various methods have already been proposed to recover at least a part of the energy contained in the pyrolysis product.

According to EP-OS No. 14 920, the pyrolysis product leaving the pyrolysis zone is chilled by indirect cooling, and the energy transferred to the coolant is utilized further within the process. For example, the sump product of a distillation column is used as the heat exchange medium and is returned to the column in reheated condition. Disadvantageously, considerable pressure losses in the area of the heat exchanger provided to chill the pyrolysis product must be tolerated in this operating mode. It is common practice to maintain the system pressure of the entire installation at the head of the hydrogen chloride column and pressure losses originating between the pyrolysis unit and the hydrogen chloride column must therefore be compensated by specifying a correspondingly higher pressure in the pyrolysis unit. Accordingly, a considerably higher pressure level and, hence, also a higher temperature level must prevail in the pyrolysis unit than would be required to per se operate the succeeding distillation units. The consequences are increased by-product formation, especially more coke formation, greater energy requirements in the pyrolysis unit, shorter service lives of the pyrolysis system, and others.

OBJECTS OF THE INVENTION

It is an object of the invention to develop a method in which the energy expended for the pyrolysis of 1,2-dichloroethane is at least partially recovered.

It is another object of the invention to conduct the product flows and design the heat exchange whereby greater pressure losses are avoided.

These and other objects and advantages of the invention will become obvious from the following detailed description.

THE INVENTION

In the novel process of treating the reaction product of pyrolysis of 1,2-dichloroethane at 10 to 14 bar to form vinyl chloride and hydrogen chloride with multiple stage cooling and distillation separation of the reaction product in a hydrogen chloride column and vinyl chloride column and recycle of unreacted 1,2-dichloroethane for the pyrolysis step, the said method being carried out at elevated pressure, the said pressure being controlled at the head of the hydrogen chloride column, the improvement consisting of dissipating within 1 sec the heat of the vaporous pyrolysis product leaving the pyrolysis zone by direct cooling by injecting liquid sump product of the downstream quench column having a temperature of from 145° C. to 165° C. into the pyrolysis product to cool it from a temperature range of 480° to 540° C. down to 150° C. to 250° C. immediately after leaving the pyrolysis zone and before entering the quench column, then charging the thus cooled product into the quench column, recovering the vapours from the head of the quench column at temperatures of 120° C. to 140° C. after having removed any coke particles from the vaporous reaction product by scrubbing the upper gas stream in the quench column by returning condensate—obtained from the indirect heat exchanger in the further processing of the 1,2-dichloroethane pyrolysis product—as reflux to the quench column with further desuperheating by evaporation of this liquid reflux forming more vapour on the top of the quench column, indirectly cooling of the vapours recovered from the head of the quench column by heat exchange to at least its condensation point in at least one indirect heat exchanger, recycling a portion of the condensed product from the indirect heat exchanger to the liquid sump product of the quench column, the heat exchange medium of each heat exchanger being at least one member of the group selected from the group consisting of (a) 1,2-dichloroethane to be fed in heated condition to the pyrolysis unit, (b) air used as combustion air to fire the pyrolysis zone, (c) the sump of the hydrogen chloride column as defined above, (d) liquid hydrogen chloride to be evaporated and, (e) water, to dissipate heat hot used within the measures according to the present invention, and thereafter separating the hydrogen chloride from the 1,2-dichloroethane pyrolysis product by fractional distillation in the hydrogen chloride column.

The pyrolysis of 1,2-dichloroethane is preferably effected at a temperature range from 480° to 540° C. at pressure from 10 to 14 bar absolute. The pressure range from 10 to 14 bar is preferred since 1,2-dichloroethan can be pre-evaporated gently in the pyrolysis unit by heat exchange with high-pressure steam of about 16 to 23 bar absolute usually available in the industry.

The reaction mixture leaving the pyrolysis zone and containing as its main components hydrogen chloride, vinyl chloride and unconverted 1,2-dichloroethane is chilled immediately after leaving the pyrolysis furnace within 1 sec, preferably within 0.5 seconds, from a temperature range of 480° to 540° C. down to a temperature of 150° to 250° C. by direct cooling before it is charged into the succeeding quench column. In the framework of the invention, direct cooling is understood to be a cooling technique whereby the heat exchange medium is caused to make direct contact with the medium to be cooled by mixing. According to the invention, the direct cooling is accomplished by injecting sump product, essentially 1,2-dichloroethane, from the quench column and the temperature of the sump product is approximately 145° to 165° C. How much sump product is to be injected is determined by the cooling effect to be achieved.

A majority of the sump product of the quench column evaporates during the direct cooling process described so that a gas/liquid mixture consisting of pyrolysis product and column sump product having a temperature of 150° to 250° C. is obtained which is charged in the lower part of the quench column. The gaseous product stream rising inside the column is washed by the counter-current of condensate obtained from the indirect heat exchanger in the further processing of the 1,2-dichloroethane pyrolysis products and charged as reflux in the upper part of the quench column, thereby removing from said product stream any coke particles formed as by-product in the pyrolysis. This effects at the same time an additional desuperheating by evaporization of this liquid reflux so that, ultimately, vapours (composed of gaseous pyrolysis product, evaporated quench liquid, and evaporated reflux liquid) of a temperature from 120° to 140° C. is obtained at the quench column head at a pressure from 9 to 12 bar absolute.

The vapours are then cooled down at least to their condensation point by indirect cooling and finally conducted to a hydrogen chloride separation column. In so doing, it is expedient to return at least a part of the condensate, essentially 1,2-dichloroethane, to the quench column as reflux to wash the product stream coming directly from the pyrolysis unit in the quench column and remove any coke particles. Indirect cooling is understood to be a technique whereby coolant and medium to be cooled are brought into indirect contact through heat exchanger surfaces, without mixing taking place.

According to the invention, the vapours are conducted through at least one, preferably at least three heat exchangers to which may be admitted different heat exchange media. Suitable heat exchange media are the sump product of the column provided for the separation of hydrogen chloride, liquid 1,2-dichloroethane fed in heated condition to the pyrolysis unit and air used as combustion air to fire the pyrolysis zone and liquid hydrogen chloride. In most cases, another heat exchanger serving to equalize the overall calorific balance is provided to dissipate heat not used within the measures according to the invention, and water may be admitted to this heat exchanger as the heat exchanger medium, for instance.

The heat from the hot pyrolysis gases obtained by the pyrolysis of 1,2-dichloroethane is thus recovered by indirect heat exchange with those media which are used in the process. This also includes the heat exchange with liquid hydrogen chloride which thereby goes into the gaseous state because a part of the large amounts of hydrogen chloride produced in the process must be buffered in liquid state for process engineering reasons known per se to smooth the product streams developing in the further use of hydrogen chloride.

Since no substantial pressure losses occur in the process described, the measures of the invention can be carried out without problems in existing plants by interposing appropriate heat exchangers. The method is economical even when at least one of the said heat exchange media is used although it is preferred to employ all the measures in combination.

Designing the heat exchangers with respect to type and size is up to the specialist's knowledge. For example, the entire amount of vapours obtained at the quench column head can be conducted through a heat exchanger charged with one of the heat exchange media named. The vapours flow is preferably divided, about 30 to 50% by volume of the vapours being cooled at least to its condensation point by heat exchange with the sump product of the hydrogen chloride column, 20 to 40% by volume with the 1,2-dichloroethane to be fed into the pyrolysis unit, and 10 to 20% by volume by heat exchange with air needed as combustion air to fire the pyrolysis zone.

The method of the invention succeeds in recovering a majority of the energy needed for the pyrolysis of 1,2-dichloroethane for further use within the process. For instance, the energy required to operate the hydrogen chloride column can be obtained completely by appropriate heat exchange with the cracking gases.

Referring now to the drawings:

The FIGURE is a flow diagram of a preferred embodiment of the process of the invention which is explained in detail in the Example.

In the following example there are described several preferred embodiments to illustrate the invention. However, it should be understood that the invention is not intended to be limited to the specific embodiments.

EXAMPLE 75 t/h of 1,2-dichloroethane were pyrolyzed to vinyl chloride and hydrogen chloride at 12.5 bar absolute and a temperature of 512° C. (measured at the pyrolysis outlet) at a 60% cracking rate. The reaction mixture leaving the pyrolysis zone was chilled to 160° C. immediately after leaving the pyrolysis furnace within 0.35 seconds by injecting 120 t/h of sump product from quench column 1. The gas/liquid mixture thus obtained by direct cooling was conducted into the lower part of quench column 1 in which an 11 bar absolute pressure was maintained. The mixture, rising inside the column, was countercurrently washed with 40 t/h of reflux from condensate collector 2, thereby removing from the mixture any coke particles. The reflux had been charged in the upper part of the column through line 8 and was evaporated, together with 30.4 t/h of condensate from condensate collector 3 which was pumped into the sump at a temperature of 100° C. The temperature of the vapours thereby obtained at the quench column head was still 124° C.

15% by volume of the vapours from the quench column was conducted through line 5 to water-cooled condenser 6 in which this part flow of the vapours was cooled to 45° C. The condensed components were separated from the gaseous components in collector 2 and the gaseous components flowed through line 33 into the upper part of hydrogen chloride column 7. 20% of the condensed phase was charged as reflux through line 8 in quench column 1 while 80% was conducted to hydrogen chloride column 7 through line 34.

25% by weight of the vapours flowed through lines 9 and 10 to heat exchanger 14 in which 75 t/h of 1,2-dichloroethane were preheated from 30° to 80° C. by heat exchange with the evaporated quench liquid and conducted to the convection zone of the pyrolysis zone through line 15. The vapours were thereby cooled to 80° C. in heat exchanger 14 with partial condensation. Another 15% by weight of the vapours reached heat exchanger 16 through lines 9 and 12, in which 32,400 kg/h of combustion air for the pyrolysis zone were preheated from 20 to 110° C. while the vapours cooled to 100° C. and partly condensed. The preheated air was then led to the pyrolysis zone burners via pipe 17.

The condensates from heat exchangers 14 and 16 were separated from the uncondensed components in collector 18 and the condensed components reached line 5 before entering condenser 6. The uncondensed components flowed from collector 18 through line 20 into line 5, also before entering condenser 6. Finally, the product stream was cooled to a temperature of 45° C. in heat exchanger 6. 5% by weight of the vapours reached, by lines 9 and 11, heat exchanger 21 to which 2.2 t/h of liquid hydrogen chloride were admitted from the buffer tank 23 through line 35. The liquid hydrogen chloride was obtained as partial head product of hydrogen chloride column 7, condensed in Freon-operated condenser 22 and fed to tank 23 through line 36. The hydrogen chloride, evaporating in heat exchanger 21, was combined through line 24 with the hydrogen, chloride flow not condensed in condenser 22. The vapours were cooled in heat exchanger 21 to a temperature of 50° C. and separated in collector 25 into condensed and uncondensed components. The separated components were subsequently conducted separately to evaporated quench liquid line 5 through lines 27 and 26, respectively, and finally cooled to 45° C. in condenser 6.

40% by weight of the vapours were fed by lines 9 and 13 to heat exchanger 28 in which the sump content of hydrogen chloride column 7 was heated by heat exchange with the vapours. These cooled the latter to 100° C. with partial condensation occuring. The condensate was pumped via collector 3 and line 29 into the lower part of quench column at 4, where it was evaporated through heat exchange with the cracking gas mixture stemming from line 31. The uncondensed components got to line 5 through line 30 and finally to condenser 6. Tube bundles were used as heat exchangers. In heat exchanger 14, the vapours flowed around the tubes and the 1,2-dichloroethane to be heated was within the tubes. In heat exchanger 16, the vapours flowed through the tubes while the air was charged on the jacket side. In the heat exchanger 21, the vapours were admitted on the jacket side while the hydrogen chloride was led through the tubes. In the heat exchanger 28 the sump product of hydrogen chloride column 7 was in the tubes while the vapours flowed through the heat exchanger jacket.

It was possible to recover 17.6 giga Joule/h of the quenching heat and even after one year of operation, no contamination of the heat exchanger surfaces could be found on the four heat exchangers. The natural pressure loss occurring in the system amounted to only 0.3 bar absolute so that, from this aspect, the total throughput through the pyrolysis system was not restricted.

Various modifications of the invention may be made without departing from the spirit or scope thereof and it should be understood that the invention is intended to be limited only as defined in the appended claims.

What we claim is:

1. In a method of treating the reaction product of pyrolysis of 1,2-dichloroethane at 10 to 14 bar to form vinyl chloride and hydrogen chloride with multiple stage cooling and distillation separation of the reaction product in a hydrogen chloride column and vinyl chloride column and recycle of unreacted 1,2-dichloroethane for the pyrolysis step, the said method being carried out at elevated pressure, the said pressure being controlled at the head of the hydrogen chloride column, the improvement consisting of dissipating within 1 sec the heat of the vaporous pyrolysis product leaving the pyrolysis zone by direct cooling by injecting liquid sump product of the downstream quench column having a temperature of from 145° C. to 165° C. into the pyrolysis product to cool it from a temperature range of 480° to 540° C. down to 150° C. to 250° C. immediately after leaving the pyrolysis zone and before entering the quench column, then charging the thus cooled product into the quench column, recovering the vapours from the head of the quench column at temperatures of 120° C. to 140° C. after having removed any coke particles from the vaporous reaction product by scrubbing the upper gas stream in the quench column by returning condensate—obtained from the indirect heat exchangers in the further processing of the 1,2-dichloroethane pyrolysis product—as reflux to the quench column with further cooling by evaporization of this liquid reflux forming more vapour on the top of the quench column, indirectly cooling of the vapours recovered from the head of the quench column by heat exchange to at least its condensation point in a plurality of indirect heat exchangers, recycling a portion of the condensed product from said indirect heat exchangers to the liquid sump product of the quench column, the heat exchange medium of each heat exchanger being at least one member of the group selected from the group consisting of
 (a) 1,2-dichloroethane to be fed in heated condition to the pyrolysis unit,
 (b) air used as combustion air to fire the pyrolysis zone,
 (c) the sump of the hydrogen chloride column as defined above,
 (d) liquid hydrogen chloride to be evaporated and,
 (e) water, to dissipate heat not used within the measures according to the present invention, and thereafter separating the hydrogen chloride from the 1,2-dichloroethane pyrolysis product by fractional distillation in the hydrogen chloride column.

* * * * *